United States Patent [19]

Jones et al.

[11] Patent Number: 5,527,953
[45] Date of Patent: Jun. 18, 1996

[54] PROCESS FOR THE MANUFACTURE OF N-PHOSPHONOMETHYLIMINODIACETIC ACID

[75] Inventors: Raymond V. H. Jones, West Lothian; Michael C. H. Standen, Clackmannan; Graham A. Rae, Edinburgh; David J. Ritchie, Falkirk, all of Scotland

[73] Assignee: Zeneca Limited, London, United Kingdom

[21] Appl. No.: 481,419

[22] PCT Filed: Jan. 6, 1994

[86] PCT No.: PCT/GB94/00018

§ 371 Date: Jul. 10, 1995

§ 102(e) Date: Jul. 10, 1995

[87] PCT Pub. No.: WO94/15939

PCT Pub. Date: Jul. 21, 1994

[30] Foreign Application Priority Data

Jan. 14, 1993 [GB] United Kingdom ............ 9300641

[51] Int. Cl.$^6$ .................................................. C07F 9/38
[52] U.S. Cl. .................................................. 562/17
[58] Field of Search .................................................. 562/17

[56] References Cited

U.S. PATENT DOCUMENTS

| 3,288,846 | 11/1966 | Irani et al. | 260/500 |
| 3,950,402 | 4/1976 | Franz | 260/502.5 |
| 5,023,369 | 6/1991 | Fields, Jr. | 562/17 |

FOREIGN PATENT DOCUMENTS 2154589  9/1985  United Kingdom.

Primary Examiner—Jose'G. Dees
Assistant Examiner—Barbara S. Frazier
Attorney, Agent, or Firm—Joel G. Ackerman

[57] ABSTRACT

A process for the manufacture of N-phosphonomethyliminodiacetic acid which comprises: 1) reacting iminodiacetic acid with phosphorous acid and a source of formaldehyde in aqueous solution in the presence of concentrated sulphuric acid; 2) filtering and recovering the N-phosphonomethyliminodiacetic acid product precipitated in stage (1); 3) recovering the filtrates from stage (2) and optionally removing a proportion of the water therefrom; 4) transferring the filtrates from stage (3) to a further reaction stage in which further iminodiacetic acid is reacted with phosphorous acid and a source of formaldehyde in the presence of sulphuric acid; and thereafter 5) repeating stages (1), (2), (3) and (4) in a plurality of re-cycles.

6 Claims, No Drawings

PROCESS FOR THE MANUFACTURE OF N-PHOSPHONOMETHYLIMINODIACETIC ACID

This application is a 371 of PCT/GB94/00018, filed Jan. 6, 1994.

This invention relates to a chemical process and in particular a process for the manufacture of N-phosphonomethyliminodiacetic acid.

N-phosphonomethyliminodiacetic acid is a known compound useful in the manufacture of N-phosphonomethylglycine and certain salts thereof which are active as herbicides.

A typical process for the preparation of N-phosphonomethyliminodiacetic acid is described in U.S. Pat. No. 3,288,846. Thus Example IV describes a process in which the hydrochloride of aminodiacetic acid (a compound referred to herein as iminodiacetic acid) in the presence of concentrated hydrochloric acid and orthophosphoric acid is heated to 100° C. and then reacted with 38% aqueous formaldehyde solution followed by paraformaldehyde. The product is described as N,N-diacetic acid aminomethylenephosphonic acid but is referred to herein as N-phosphonomethyliminodiacetic acid.

Many other processes for the manufacture of N-phosphonomethyliminodiacetic acid are known, including for example that described in United Kingdom Patent No 2 154 589 in which an alkali metal salt of iminodiacetic acid such as the sodium salt is reacted with a strong mineral acid such as sulphuric acid to form the strong mineral acid salt of iminodiacetic acid and the alkali metal salt of the acid (for example sodium sulphate). The strong mineral acid salt of iminodiacetic acid is then reacted with formaldehyde and phosphorous acid and sufficient water to dissolve the alkali metal salt whilst the N-phosphonomethyliminodiacetic acid product is precipitated.

We have now found that, surprisingly, the filtrates from the reaction of iminodiacetic acid with phosphorous acid and formaldehyde may be re-cycled a plurality of times without excessive build-up of by-product, provided that sulphuric acid is used as mineral acid and provided that the starting material is iminodiacetic acid and not an alkali metal salt thereof.

According to the present invention there is provided a process for the manufacture of N-phosphonomethyliminodiacetic acid which comprises:

1) reacting iminodiacetic acid with phosphorous acid and a source of formaldehyde in aqueous solution in the presence of concentrated sulphuric acid;

2) filtering and recovering the N-phosphonomethyliminodiacetic acid product precipitated in stage (1);

3) recovering the filtrates from stage (2) and optionally removing a proportion of the water therefrom;

4) transferring the filtrates from stage (3) to a further reaction stage in which further iminodiacetic acid is reacted with phosphorous acid and a source of formaldehyde in the presence of sulphuric acid; and thereafter 5) repeating stages (1), (2), (3) and (4) in a plurality of re-cycles.

The process of the present invention is well adapted to be operated in a continuous manner, especially at large manufacturing volumes. It is to be understood therefore that stages (1) to (5) above may represent hypothetical stages in a continuous reaction wherein filtrate stream is continuously re-cycled to the reaction vessel (optionally via a water removal stage) and wherein reactants are continuously charged to the reaction vessel and N-phosphonomethyliminodiacetic acid product which precipitates is removed by continuous or semi-continuous filtration.

The use of the re-cycle reaction of the present invention will generally have the effect of reducing the waste/effluent stream produced in the process and of making most effective use of the starting materials.

The source of formaldehyde is suitably either an aqueous solution of formaldehyde or paraformaldehyde, depending on the proportion of water which is desired to be added. If water is removed from the filtrates in stage (3), it may be desirable to use paraformaldehyde in subsequent reaction stages (1), thereby reducing the proportion of water which it is necessary to remove.

The phosphorous acid may be introduced into the reaction as a solid (for example as a flaked solid), as a molten liquid or as an aqueous solution, for example as a commercially available aqueous solution typically containing 70% by weight of phosphorous acid.

Preferably water is removed in stage (3) and suitable methods for the removal of water include for example distillation of the filtrates from stage (2) or the use of semi-permeable media. The distillation of the filtrates may take place at atmospheric pressure at the boiling point of the filtrate medium, typically of the order of 140° C. by the time the distillation is completed. We have found that distillation at atmospheric pressure is satisfactory and permits multiple re-cycles. It may however, be desirable to reduce the possible formation of by-products by operating the distillation stage under reduced pressure and at a correspondingly lower boiling point of the filtrate medium. The possibility of a reduced formation of by-products must be offset against the added cost of operation at reduced pressure. In general however, it is preferred that the distillation of the filtrate medium takes place at a temperature of from 20° C.–140° C., for example 60° C.–140° C., and especially from 60° C.–90° C. or more particularly from 40° C. to 100° C., the pressure being reduced accordingly.

If desired, the solid N-phosphonomethyliminodiacetic acid product which is recovered by filtration from stage (1) may be washed to remove filtrate medium adhering thereto. If desired at least a proportion of such washings may be added to the filtrates and the term "filtrates" and "flitrate medium" as used herein is to be understood to include such washings if present. It is to be noted however, that the addition of washing to the filtrates will increase the proportion of water which is to be optionally removed in stage (3) and that the addition of the washings to the filtrate stream may not always therefore be desirable.

At least a proportion of any formaldehyde present in the filtrates may be removed during the distillation stage (if present). If desired, formaldehyde may be recovered during the distillation stage and may be returned to the reaction stage (1). However, the re-cycle of formaldehyde is not necessary and does not form an essential part of the present invention.

The reaction conditions used during the reaction stage (1) are essentially conventional. Substantially stoichiometric proportion of reactants may be used although it may be desirable to use a slight molar excess relative to iminodiacetic acid. Thus it is preferred to use from 1–1.5 moles of phosphorious acid per mole of iminodiacetic acid, for example 1.1 mole of phosphorous acid per mole of iminodiacetic acid. Similarly, it is preferred to use from 1–2 moles of formaldehyde per mole of iminodiacetic acid, for example 1.2 mole of formaldehyde per mole of iminodiacetic acid. Sulphuric acid is not consumed as a primary reactant during the reaction and sufficient sulphuric acid should be used to provide an appropriate reaction rate. Thus it is preferred to use from 0.5–2 moles of sulphuric acid per mole of iminodiacetic acid, for example about 1 mole of sulphuric acid per mole of iminodiacetic acid.

Sufficient water should be used to ensure a mobile reaction medium. In general up to 10 or more moles of water per mole of iminodiacetic acid may be used, but the proportion of water necessary to provide an effective reaction medium may be readily determined by those skilled in the art.

In the reaction stage (1) of the process of the present invention it is preferred to add the source of formaldehyde to a pre-mixture of the iminodiacetic acid, phosphorous acid and sulphuric acid. If aqueous formaldehyde is used as the source of formaldehyde, water will be added with the formaldehyde. A typical commercially available aqueous formaldehyde solution contains for example from about 36% w/w to 50% w/w formaldehyde together with for example about 0.5–15% w/w methanol as stabiliser. If such a solution is used for example at a ratio of 1 mole of formaldehyde per mole of iminodiacetic acid, approximately 1.7–3 moles of water will be added per mole of iminodiacetic acid. It may then be sufficient to add no water to the pre-mixture of the iminodiacetic acid, phosphorous acid and sulphuric acid. In general however it is preferred to add water to the pre-mixture such that the total proportion of water, including any water added with the source of formaldehyde or with the phosphorous acid, is up to 10 moles of water per mole of iminodiacetic acid. If paraformaldehyde is used as the source of formaldehyde no water or methanol is added with the formaldehyde and the desired proportion of water is added to the pre-mixture.

The reaction temperature is typically from 50° C. to 150° C., for example from 105° C. to 125° C. or more particularly from 110° C. to 120° C. Lower reaction temperatures, for example reaction temperatures below 100° C., may have the advantage of reducing the level of any by-products formed during the reaction but this will tend to be offset by a reduced rate of reaction. It then may be advantageous to adjust the process conditions in favour of an increased reaction rate, for example by increasing the proportion of sulphuric acid in the reaction mixture.

The proportions of further iminodiacetic acid, phosphorous acid, sulphuric acid and formaldehyde added to the further reaction stage(s) (1) following the re-cycle of the filtrates via stages (4) and (5) will of course depend on the proportions of the reactants returned via re-cycle and will be selected to retain the total proportion of reactants within the desired ranges. Similarly, the proportion of water removed during stage (3), for example by the distillation of the filtrates will be selected generally to maintain the desired overall water balance and the desired concentrations of the reactants in the aqueous medium.

Whilst the process of the present invention provides for the option of multiple re-cycles, it is inevitable that by-products may progressively build up as re-cycle continues. It is of course perfectly possible to continue the re-cycle until an excessive level of by-products builds up. In general however, it is preferred to compensate for the build up of any by-products by operating a purge of the filtrates stream in which a proportion of the filtrates stream is removed on each cycle. A purge of for example from up to 25% to 40% or more of the filtrates stream may be used but in general it is preferred not to use a purge stream greater than 50% and a purge stream of up to 40% of the filtrates stream may be typical, although of course it may be possible to reduce the level of any by-products (as described herein) such that even lower purge levels may be used or even no purge at all. A corresponding purge stream may be used in continuous operation.

The invention is illustrated by the following Examples in which all parts and percentages are by weight unless otherwise stated.

EXAMPLE 1

Cycle 1

Water (17.3 g, 0.961 moles) was charged to a 250 ml three neck flask fitted with thermometer, condenser, dropping funnel and stirrer. Phosphorous acid (42.6 g, 0.514 moles), sulphuric acid (50.0 g, 0.500 moles—added over 10 minutes during which an exotherm from 20° C. to 60° C. was observed) and iminodiacetic acid (66.5 g, 0.490 moles) were added to the stirred reaction flask. The reaction mixture was then heated to 120° C. and formaldehyde (48.2 g at 36.1% strength, 0.580 moles) was added over one hour. The temperature was maintained between 110° and 120° C. during addition. On complete addition, the reaction mixture was allowed to cool to 25° C. over 90 minutes and the reaction mixture was filtered. The filter cake was washed with water (57 ml) and the product was dried in a vacuum oven to yield 67.9 g of N-phosphonomethyliminodiacetic acid at 98.0% strength, equivalent to an isolated yield of 59.8%. The filtrates (128.0 g) and the water wash (66.0 g) were analysed at 13.7% and 5.5% N-phosphonomethyliminodiacetic acid respectively. This was equivalent to a total conversion yield of 78.9% N-phosphonomethyliminodiacetic acid.

Filtrates Distillation

The filtrates (122.3 g) from Cycle 1 were recharged to the reaction flask and the apparatus was adapted for distillation. The filtrates were heated to boiling point and 27 g of distillate was removed taking the final temperature of the pot contents to 140° C. The concentrated filtrates were then used in Cycle 2.

Cycle 2

Concentrated filtrates from Cycle 1 were charged to a 500 ml three neck flask fitted with thermometer, condenser, dropping funnel and stirrer. Phosphorous acid (40.8 g, 0.493 moles), iminodiacetic acid (63.6 g, 0.469 moles) and sulphuric acid (5.0 g, 0.050 moles) were added, with stirrring, to the flask (sulphuric acid was charged on the assumption that 10% of the sulphuric acid was lost in the wash and filter cake). The reaction mixture was then heated to 120° C. and formaldehyde (46.1 g at 36.1% strength, 0.555 moles) was then added over one hour. The temperature was maintained between 110° and 120° C. during addition. On complete addition the reaction mixture was allowed to cool to 25° C. over 90 minutes. The reaction mixture was filtered and the filter cake washed with water (57 ml). The product was dried in a vacuum oven to yield 102.2 g of N-phosphonomethyliminodiacetic acid at 95.4% strength equivalent to a cumulative isolated yield of 75.3%. The filtrates (99.3 g) and the water wash (76.8 g) were analysed at 7.5% and 3.7% N-phosphonomethyliminodiacetic acid respectively. This was equivalent to a total cumulative conversion yield of 81.7% N-phosphonomethyliminodiacetic acid.

Filtrates Distillation

The filtrates (95.1 g) from reaction 1 were recharged to the reaction flask and the apparatus was adapted for distillation. The filtrates were heated to boiling point and 20.5 g of distillate was removed taking the final pot temperature to 140° C. The concentrated filtrates were then used in Cycle 3.

Cycle 3

Concentrated filtrates from reaction 2 was charged to a 250 ml three neck flask fitted with thermometer, condenser, dropping funnel and stirrer. Phosphorous acid (39.1 g, 0.472 moles), iminodiacetic acid (60.9 g, 0.449 moles) and sulphuric acid (4.79 g, 0.0479 moles) were added, with stirring, to the flask. The reaction mixture was then heated to 120° C. and formaldehyde (44.2 g at 36.1% strength, 0.533 moles) was then added over one hour. The temperature was maintained between 110° and 120° C. during addition. On complete addition the reaction mixture was allowed to cool to 25° C. over 90 minutes. The reaction mixture was filtered and the filter cake washed with water (57 ml). The product was dried in a vacuum oven to yield 90.1 g of N-phosphonomethyliminodiacetic acid at 95.6% strength equivalent to a cumulative isolated yield of 78.2%. The filtrates (91.1 g) and the water wash (71.8 g) were analysed at 5.0% and 3.0% N-phosphonomethylimiodiacetic acid respectively. This was equivalent to a total cumulative conversion yield of 82.3% N-phosphonomethyliminodiacetic acid.

Filtrates Distillation

The filtrates (88.3 g) from Cycle 3 were recharged to the reaction flask and were distilled as previously to remove 20.0 g of distillate.

Cycle 4

Concentrated filtrates from Cycle 3 were charged to a 250 ml three neck flask fitted with therometer, condenser, dropping funnel and stirrer. Phosphorous acid (37.9 g, 0.457 moles), iminodiacetic acid (59.0 g, 0.434 moles) and sulphuric acid (4.64 g, 0.046 moles) were added, with stirring, to the flask. The reaction mixture was then heated to 120° C. and formaldehyde (42.8 g at 36.1% strength, 0.515 moles) was then added over one hour and sulphuric acid (4.64 g, 0.046 moles) were added, with stirring, to the flask. The reaction mixture was then heated to 120° C. and formaldehyde (42.8 g at 36.1% strength, 0.515 moles) was then added over one hour. The temperature was maintained between 110° and 120° C. during addition. On complete addition the reaction mixture was allowed to cool to 25° C. over 90 minutes. The reaction mixture was filtered and the filter cake washed with water (57 ml). The product was dried in a vacuum oven to yield 66.2 g of N-phosphonomethyliminodiacetic acid at 91.4% strength equivalent to a cumulative isolated yield of 74.2%. The filtrates (92.8 g) and the water wash (70.7 g) were analysed at 5.4% and 4.2% N-phosphonomethyliminodiacetic acid respectively. This was equivalent to total cumulative conversion yield of 78.2% N-phosphonomethyliminodiacetic acid.

In Example 1, a proportion of the filtrates in each cycle was removed for anlysis. Subsequent reactions were scaled down accordingly.

Cumulative yields are calculated using the following equations.

$$\text{Cumulative isolated yield} = \frac{\overset{n}{\Sigma}(M\ PIDA\ \text{ISO})}{\overset{n}{\Sigma}(M\ \text{iminodiacetic acid})} \times 100$$

Cumulative conversion yield =

$$\frac{(M\ PIDA\ \text{in}\ n\ \text{th}\ FILTS) + \overset{n}{\Sigma}(M\ PIDA\ \text{ISO}) + \overset{n}{\Sigma}M\ PIDA\ \text{WASH})}{\overset{n}{\Sigma}(M\ \text{iminodiacetic acid})} \times 100$$

Where:

"M" is the number of moles.

"PIDA ISO" is isolated N-phosphonomethyliminodiacetic acid.

"PIDA WASH" is N-phosphonomethyliminodiacetic acid in wash

"n th" is the number of recycles (n=0–3).

"$n_\Sigma$" is to SUM from n=0 to n=n.

It should be noted that for each cycle, only the initial filtrate was carried forward to the next stage, leaving any mother liquor in the filter cake as an effective purge of approximately 25%.

EXAMPLE 2

Cycle 1

Water (11.2 g, 0.623 moles) was charged to a 500 ml three neck flask fitted with thermometer, condenser, dropping funnel and stirrer. The stirrer was started and phosphorous acid (42.6 g, at 99%; 0.514 moles) was added whereupon the temperature dropped from 20° C. to 12° C. Sulphuric acid (49.8 g at 98%, 0.498 moles) was then added over 10 minutes whilst maintaining the temperature below 50° C. with a water bath. Iminodiacetic acid (66.5 g at 95.4% strength, 0.479 moles) was then added to the reaction flask. The reaction mixture was heated to 115° C. and formaldehyde (48.2 g at 37.0% strength, 0.594 moles) was added over two hours. The temperature was maintained between 110° and 120° C. during addition. On complete addition, the reaction mixture was held at 115° C. for a furthre hour and then allowed to cool to 90° C. A second water charge (92.0 g) was added over 1 hour maintaining the temperature at approximately 90° C. during the addition. The reaction mixture was allowed to self-cool overnight. The slurry was filtered, washed with cold water (57.0 g) and the resulting product was dried at 60° C. in a vacuum oven overnight to give 100.2 g of N-phosphonomethyliminodiacetic acid at 95.7% strength, equivalent to an isolated yield of 88.1%. The filtrates (172.8 g) and the water wash (71.7 g) contained 4.8% and 1.2% N-phosphonomethyliminodiacetic acid respectively. This gave a total conversion yield of 93.5% N-phosphonomethyliminodiacetic acid.

The combined filtrates and wash liquors (236.0 g) were charged to a stirred 500 ml flask set up for vacuum distillation. The equipment was evacuated to a pressure of 50 mm Hg and gradually warmed to distill off water until the flask temperature rose to 100° C. The residue (71.6 g) was cooled and analysed for N-phosphonomethyliminodiacetic acid (9.1%) and moisture content (14.9%).

Cycle 1

(Summary Table)

| MATERIAL | Actual Weight | Strength | 100% Weight | MOLES | MOLE RATIO |
|---|---|---|---|---|---|
| Iminodiacetic acid | 66.5 | 95.8 | 63.7 | 0.479 | 1 |
| Water | 11.2 | 100 | 11.2 | 0.622 | 1.3 |
| Phosphorous acid | 42.6 | 99.0 | 42.2 | 0.514 | 1.07 |
| Sulphuric acid | 49.8 | 98.0 | 48.8 | 0.498 | 1.04 |
| Formaldehyde solution | 48.2 | 37.0 | 17.8 | 0.594 | 1.24 |
| Water (dilution) | 92.0 | | | | |
| Water (wash) | 57.0 | | | | |

Cycle 2

Concentrated filtrate and wash liquor (66.8 g, equivalent to 90% of the original quantity before removal of samples and containing moisture (10 g) and N-phosphonomethyliminodiacetic acid (6.08 g, 0.027 moles)) was charged with extra water (1.2 g, to make a total of 11.2 g, 0.622 moles) to the reaction flask described above, and phosphorous acid (39.7 g at 99%, 0.479 moles) was added. Sulphuric acid (10% replacement, i.e. 5.0 g at 98%, 0.05 moles) was added over 5 minutes, followed by iminodiacetic acid (66.5 g at 95.4%, 0.479 moles). The procedure of cycle 1 was then followed to yield 107.6 g of dry product at 98.9% strength, equivalent to an isolated yield of 97.9%. The filtrate (179.6 g) and wash (54.8 g) contained 2.61% and 1.66% N-phosphonomethyliminodiacetic acid respectively; the total yield, minus the N-phosphonomethyliminodiacetic acid recycled with the filtrate, gave a stage conversion yield of 97.4%.

Cycle 2 with 90% Acid Filtrates Recycle (Summary Table)

| MATERIAL | Actual Weight | Strength | 100% Weight | MOLES | MOLE RATIO |
|---|---|---|---|---|---|
| Concentrated filtrates | 66.8 | | | | |
| Iminodiacetic acid | 66.5 | 95.8 | 63.7 | 0.479 | 1 |
| Water: see text: To | 11.2 | 100 | 11.2 | 0.622 | 1.3 |
| Phosphorous acid | 39.7 | 99.0 | 39.3 | 0.479 | 1 |
| Sulphuric acid | 5.0 | 98.0 | 4.9 | 0.050 | 0.1 |
| Formaldethyde solution | 48.2 | 37.0 | 17.8 | 0.594 | 1.24 |
| Water (dilution) | 92.0 | | | | |
| Water (wash) | 75.0 | | | | |

Cycles 3 to 8

The procedure as for Cycle 2 was repeated for Cycles 3 to 8, adjustments being made for the water content of the concentrated filtrate (equivalent to 90% recycle in each case), as follows. The abbreviation PIDA is used for N-phosphonomethyliminiodiacetic acid.

| | Concentrated Filtrate + Wash | | | | Isolated Product | | Conversion |
|---|---|---|---|---|---|---|---|
| Cycle No. | Weight used g | Water content % | PIDA content % | Water Added g | Strength % | Yield % | Yield % |
| 3 | 67.2 | 12.9 | 8.2 | 2.5 | 96.4 | 92.3 | 93.4 |
| 4 | 71.3 | 10.5 | 9.2 | 3.7 | 94.8 | 89.8 | 89.3 |
| 5 | 75.8 | 7.7 | 7.6 | 5.4 | 94.3 | 90.2 | 89.6 |
| 6 | 81.3 | 8.9 | 6.2 | 4.0 | 96.6 | 87.5 | 89.7 |
| 7 | 90.7 | 7.8 | 8.1 | 4.1 | 96.1 | 87.5 | 86.6 |
| 8 | 96.8 | 6.2 | 6.3 | 5.2 | 96.6 | 80.0 | 81.2 |

Cycle 1

(Summary Table)

| MATERIAL | Actual Weight | Strength | 100% Weight | MOLES | MOLE RATIO |
|---|---|---|---|---|---|
| Iminodiacetic acid | 66.5 | 95.8 | 63.7 | 0.479 | 1 |
| Water | 11.2 | 100 | 11.2 | 0.622 | 1.3 |
| Phosphorous acid | 42.6 | 99.0 | 42.2 | 0.514 | 1.07 |
| Sulphuric acid | 49.8 | 98.0 | 48.8 | 0.498 | 1.04 |
| Formaldehyde solution | 48.2 | 37.0 | 17.8 | 0.594 | 1.24 |
| Water (dilution) | 92.0 | | | | |
| Water (wash) | 57.0 | | | | |

The procedure of Cycle 1 of Example 2 was followed using the above proportions.

The resultant slurry was filtered, washed with cold water (57.0 g) and the resulting product was dried at 60° C. in a vacuum oven overnight to give 102.2 g of N-phosphonomethyliminodiacetic acid at 95.6% strength, equivalent to an isolated yield of 89.6%. The filtrates (172.0 g) and the water wash (64.4 g) contained 1.71% and 1.17% N-phosphonomethyliminodiacetic acid respectively. This gave a total conversion yield of 93.0% N-phosphonomethyliminodiacetic acid.

The combined filtrates and wash liquors (229.0 g) were charged to a stirred 500 ml flask set up for vacuum distillation. The equipment wa evacuated to a pressure of 50 mm Hg and gradually warmed to distill off water until the flask temperature rose to 100° C. The residue (72.6 g) was cooled and analysed for N-phosphonomethyliminodiacetic acid (7.1%) and moisture content (17.6%)

Cycle 2 with 100% Acid Filtrates Recycle (Summary Table)

| MATERIAL | Actual Weight | Strength | 100% Weight | MOLES | MOLE RATIO |
|---|---|---|---|---|---|
| Concentrated filtrates | 70.0 | | | | |
| Iminodiacetic acid | 62.2 | 95.8 | 59.6 | 0.448 | 1 |
| Water: See text | | | | | |
| Phosphorous acid | 37.1 | 99.0 | 36.7 | 0.448 | 1 |

-continued (Summary Table)

| MATERIAL | Actual Weight | Strength | 100% Weight | MOLES | MOLE RATIO |
|---|---|---|---|---|---|
| Sulphuric acid | 0.9 | 98.0 | 0.9 | 0.009 | 0.02 |
| Formaldehyde solution | 45.0 | 37.0 | 16.7 | 0.555 | 1.24 |
| Water (dilution) | 84 | | | | |
| Water (wash) | 53 | | | | |

Procedure

Concentrated filtrate and wash liquor (70.0 g, containing moisture (12.3 g) and N-phosphonomethyliminodiacetic acid (4.97 g)) was charged the reaction flask and phosphorous acid (37.1 g at 99%, 0.448 moles) was added. Sulphuric acid (2% nominal replacement, i.e. 0.9 g at 98%, 0.009 moles) was added followed by iminodiacetic acid (62.2 g at 95.4%, 0.448 moles). The reaction mixture was heated to 115° and formaldehyde (45.0 g at 37% strength, 0.555 moles) was added over 2 hours. The reactant quantities were calculated so as to make the concentrated filtrates usage equivalent to 100% recycle before removal of samples for analysis. The standard procedure of Examle 2 was then followed, using 84 g water for dilution and 53 g water for washing the filter paste, to yield 100.4 g of dry product at 96.8% strength, equivalent to an isolated yield of 95.6%. The filtrate (167.0 g) and wash (49.0 g) contained 2.03% and 1.5% N-phosphonomethyliminodiacetic acid respectively; the total yield, minus the N-phosphonomethyliminodiacetic acid recycled with the concentrated filtrate charge, gave a stage conversion yield of 94.6%.

Cycles 3 to 8

The procedure as for Cycle 2 was repeated for Cycles 3 to 8, adjustments being made for the water content in the initial mixture before formaldehyde addition being adjusted wherever possible to 1.3 moles per mole of IDAA.

The details are shown below:

| | | Concentrated Filtrate + Wash | | | | Isolated Product | | Conversion |
|---|---|---|---|---|---|---|---|---|
| Cycle No. | Scale (Moles IDAA) | Weight used g | Water content % | PIDA content % | Water Added g | Strength % | Yield % | Yield % |
| 3 | 0.423 | 68.6 | 14.5 | 6.6 | Nil | 92.8 | 89.9 | 90.3 |
| 4 | 0.388 | 67.6 | 13.7 | 8.0 | Nil | 94.1 | 91.0 | 89.7 |
| 5 | 0.352 | 71.4 | 19.9 | 6.9 | Nil | 93.8 | 88.6 | 87.5 |
| 6 | 0.324 | 66.5 | 10.7 | 6.2 | 0.5 | 91.8 | 84.0 | 83.0 |
| 7 | 0.293 | 68.5 | 11.5 | 6.7 | Nil | 95.6 | 82.3 | 80.9 |
| 8 | 0.260 | 69.7 | 7.1 | 5.3 | Nil | 89.2 | 62.0 | 55.8 |

Note: The fact that conversion yields appear, after the third cycle, always to be lower than isolated yields, is probably due to the difficulty of estimating N-phosphonomethyliminodiacetic acid in relatively impure filtrate samples.

EXAMPLE 4

Cycle 1

(Summary Table)

| MATERIAL | Actual Weight | Strength | 100% Weight | MOLES | MOLE RATIO |
|---|---|---|---|---|---|
| Iminodiacetic acid | 66.5 | 95.8 | 63.7 | 0.479 | 1 |
| Water | 11.2 | 100 | 11.2 | 0.622 | 1.3 |
| Phosphorous acid | 42.6 | 99.0 | 42.2 | 0.514 | 1.07 |
| Sulphuric acid | 49.8 | 98.0 | 48.8 | 0.498 | 1.04 |
| Formaldehyde solution | 48.2 | 37.0 | 17.8 | 0.594 | 1.24 |
| Water (dilution) | 92.0 | | | | |
| Water (wash) | 57.0 | | | | |

The procedure of Cycle 1 of Example 2 was followed using the above proportions.

The resultant slurry was filtered, washed with cold water (57.0 g) and the resulting product was dried at 60° C. in a vacuum oven overnight to give 103.1 g of N-phosphonomethyliminodiacetic acid at 98.0% strength, equivalent to an isolated yield of 91.2%. The filtrates (178.2 g) and the water wash (56.3 g) contained 3.6% and 1.8% N-phosphonomethyliminodiacetic acid respectively. This gave a total conversion yield of 98.0% N-phosphonomethyliminodiacetic acid.

The combined filtrates and wash liquors (224.2 g) were charged to a stirred 500 ml flask set up for vacuum distillation. The equipment wa evacuated to a pressure of 4–25 mm Hg and gradually warmed to distill off water until the flask temperature rose to 100° C. The residue (70.2 g) was cooled and analysed for N-phosphonomethyliminodiacetic acid (11.3%) and moisture content (15.3%).

Cycle 2 with 62.5% Acid Filtrates Recycle

| MATERIAL | Actual Weight | Strength | 100% Weight | MOLES | MOLE RATIO |
|---|---|---|---|---|---|
| Concentrated filtrates | 45.8 | | | | |
| Iminodiacetic acid | 66.5 | 95.3 | 63.7 | 0.479 | 1 |
| Water: See text: | 11.2 | 100 | 11.2 | 0.622 | 1.3 |

| MATERIAL | Actual Weight | Strength | 100% Weight | MOLES | MOLE RATIO |
|---|---|---|---|---|---|
| To Phosphorous acid | 39.7 | 99.0 | 39.3 | 0.479 | 1 |
| Sulphuric acid | 18.7 | 98.0 | 18.3 | 0.187 | 0.39 |
| Formaldehyde solution | 48.2 | 37.0 | 17.8 | 0.594 | 1.24 |
| Water (dilution) | 92.0 | | | | |
| Water (wash) | 57.0 | | | | |

Procedure

Concentrated filtrate and wash liquor (45.8 g, equivalent to 62.5% of the original quantity before removal of samples, contianing moisture (7.0 g ) and N-phosphonomethyliminodiacetic acid (5.2 g, 0.023 moles)) was charged with extra water (4.2 g, to make a total of 11.2 g, 0.622 moles) to the reaction flask described above, and phosphorous acid (39.7 g at 99%, 0.479 moles) was added. Sulphuric acid (37.5% replacement, i.e. 18.7 g at 98%, 0.187 moles) was added over 5 minutes, followed by iminodiacetic acid (66.5 g at 95.4%, 0.479 moles). The above procedure was then followed to yield 106.3 g of dry product at 100% strength equivalent to an isolated yield of 97.8%. The filtrate (184.8 g) and wash 55.6 g) contained 2.2% and 1.3% N-phosphonomethyliminodiacetic acid respectively; the total yield, minus the N-phosphonomethyliminodiacetic acid recycled with the filtrate, gave a stage conversion yield of 97.4%.

Cycles 3 to 8

The procedure as for Cycle 2 was repeated for Cycles 3 to 8, adjustments being made for the water content of the concentrated filtrates (equivalent to 62.5% recycle in each case) as follows:

| | Concentrated Filtrate + Wash | | | | Isolated Product | | Conversion |
|---|---|---|---|---|---|---|---|
| Cycle No. | Weight used g | Water content % | PIDA content % | Water Added g | Strength % | Yield % | Yield % |
| 3 | 45.5 | 16.1 | 7.1 | 3.9 | 98.9 | 91.4 | 95.2 |
| 4 | 47.5 | 10.4 | 10.4 | 6.3 | 96.3 | 92.1 | 93.2 |
| 5 | 46.1 | 8.4 | 7.8 | 6.3 | 95.4 | 90.7 | 92.2 |
| 6 | 48.3 | 7.5 | 7.3 | 7.6 | 96.9 | 90.6 | 92.6 |
| 7 | 49.4 | 8.5 | 9.4 | 7.0 | 96.9 | 88.3 | 90.8 |
| 8 | 51.1 | 7.8 | 10.5 | 7.2 | 99.6 | 93.5 | 95.1 |

EXAMPLE 5

Cycle 1

(Summary Table)

| MATERIAL | Actual Weight | Strength | 100% Weight | MOLES | MOLE RATIO |
|---|---|---|---|---|---|
| Iminodiacetic acid | 66.5 | 95.8 | 63.7 | 0.479 | 1 |
| Water | 11.2 | 100 | 11.2 | 0.622 | 1.3 |
| Phosphorous acid | 42.6 | 99.0 | 42.2 | 0.514 | 1.07 |
| Sulphuric acid | 49.8 | 98.0 | 48.8 | 0.498 | 1.04 |
| Formaldehyde solution | 48.2 | 37.0 | 17.8 | 0.594 | 1.24 |
| Water (dilution) | 92.0 | | | | |
| Water (wash) | 57.0 | | | | |

The procedure of Cycle 1 of Example 2 was followed using the above proportions.

The resultant slurry was filtered, washed with cold water (57.0 g) and the resulting product was dried at 60° C. in a vacuum oven overnight to give 102.2 g of N-phosphonomethyliminodiacetic acid at 97.3% strength, equivalent to an isolated yield of 91.5%. The filtrates (175.4 g) and the water wash (57.9 g) contained 1.9% and 1.2% N-phosphonomethyliminodiacetic acid respectively. This gave a total conversion yield of 95.2% N-phosphonomethyliminodiacetic acid.

The combined filtrates and wash liquors (227.8 g) were charged to a stirred 500 ml flask set up for vacuum distillation. The equipment wa evacuated to a pressure of 50 mm Hg and gradually warmed to distill off water until the flask temperature rose to 100° C. The residue (68.8 g) was cooled and analysed for N-phosphonomethyliminodiacetic acid (6.5%) and moisture content (14.2%).

Cycle 2 with 95% Acid Filtrates Recycle (Summary Table)

| MATERIAL | Actual Weight | Strength | 100% Weight | MOLES | MOLE RATIO |
|---|---|---|---|---|---|
| Concentrated filtrates | 66.9 | | | | |
| Iminodiacetic acid | 66.5 | 95.3 | 63.7 | 0.479 | 1 |
| Water: See text: To | 11.2 | 100 | 11.2 | 0.622 | 1.3 |
| Phosphorous acid | 39.7 | 99.0 | 39.3 | 0.479 | 1 |
| Sulphuric acid | 2.5 | 98.0 | 2.4 | 0.025 | 0.05 |
| Formaldehyde solution | 48.2 | 37.0 | 17.8 | 0.594 | 1.24 |
| Water (dilution) | 92.0 | | | | |
| Water (wash) | 57.0 | | | | |

Procedure

Concentrated filtrate and wash liquor (66.9 g, equivalent to 95% of the original quantity before removal of samples, containing moisture (9.5 g) and N-phosphonomethyliminodiacetic acid (4.35 g, 0.019 moles)) was charged with extra water (1.7 g, to make a total of 11.2 g, 0.622 moles) to the reaction flask described above, and phosphorous acid (39.7 g at 99%, 0.479 moles) was added. Sulphuric acid (5% replacement, i.e. 2.5 g at 98%, 0.025 moles) was added over 5 minutes, followed by iminodiacetic acid (66.5 g at 95.4%, 0.479 moles). The above procedure was then followed to yield 104.5 g of dry product at 95.1% strength equivalent to an isolated yield of 91.4%. The filtrate (192.3 g) and wash (51.6 g) contained 2.5% and 1.2% N-phosphonomethyliminodiacetic acid respectivvely; the total yield, minus the N-phosphonomethyliminodiacetic acid recycled with the filtrate, gave a stage conversion yield of 92.5%.

Cycles 3 to 8

The procedure as for Cycle 2 was repeated for Cycles 3 to 8, adjustments being made for the water content of the concentrated filtrates (equivalent to 95% recycle in each case) as follows:

| Cycle No. | Concentrated Filtrate + Wash Weight used g | Water content % | PIDA content % | Water Added g | Isolated Product Strength % | Isolated Product Yield % | Conversion Yield % |
|---|---|---|---|---|---|---|---|
| 3 | 78.8 | 21.4 | 7.3 | Nil | 94.1 | 90.1 | 89.1 |
| 4 | 83.2 | 17.9 | 6.7 | Nil | 94.4 | 90.7 | 90.4 |
| 5 | 89.6 | 17.0 | 6.7 | Nil | 93.5 | 88.2 | 87.9 |
| 6 | 92.6 | 12.5 | 3.9 | Nil | 94.7 | 89.5 | 90.8 |
| 7 | 95.6 | 10.7 | 6.1 | 0.4 | 94.7 | 81.4 | 79.6 |
| 8 | 108.2 | 12.2 | 3.2 | Nil | 85.0 | 54.2 | 52.2 |

EXAMPLE 6

Cycle 1

(Summary Table)

| MATERIAL | Actual Weight | Strength | 100% Weight | MOLES | MOLE RATIO |
|---|---|---|---|---|---|
| Iminodiacetic acid | 66.5 | 95.8 | 63.7 | 0.479 | 1 |
| Water | 11.2 | 100 | 11.2 | 0.622 | 1.3 |
| Phosphorous acid | 42.6 | 99.0 | 42.2 | 0.514 | 1.07 |
| Sulphuric acid | 49.8 | 98.0 | 48.8 | 0.498 | 1.04 |
| Formaldehyde solution | 48.2 | 37.0 | 17.8 | 0.594 | 1.24 |
| Water (dilution) | 92.0 | | | | |
| Water (wash) | 57.0 | | | | |

The procedure of Cycle 1 of Example 2 was followed using the above proportions.

The resultant slurry was filtered, washed with cold water (57.0 g) and the resulting product was dried at 60° C. in a vacuum oven overnight to give 98.8 g of N-phosphonomethyliminodiacetic acid at 95.8% strength, equivalent to an isolated yield of 87.5%. The filtrates (165.7 g) and the water wash (69.0 g) contained 2.5% and 1.67% N-phosphonomethyliminodiacetic acid respectively. This gave a total conversion yield of 92.35% N-phosphonomethyliminodiacetic acid.

The combined filtrates and wash liquors (222.2 g) were charged to a stirred 500 ml flask set up for vacuum distillation. The equipment wa evacuated to a pressure of 40 mm Hg and gradually warmed to distill off water until the flask temperature rose to 100° C. The residue (71.1 g) was cooled and analysed for N-phosphonomethyliminodiacetic acid (10.3%) and moisture content (17.1%).

Cycle 2 with 75% Acid Filtrates Recycle (Summary Table)

| MATERIAL | Actual Weight | Strength | 100% Weight | MOLES | MOLE RATIO |
|---|---|---|---|---|---|
| Concentrated filtrates | 56.3 | | | | |
| Iminodiacetic acid | 66.5 | 95.8 | 63.7 | 0.479 | 1 |
| Water: See text: To | 11.2 | 100 | 11.2 | 0.622 | 1.3 |
| Phosphorous acid | 39.7 | 99.0 | 39.3 | 0.479 | 1 |
| Sulphuric acid | 12.0 | 98.0 | 11.8 | 0.120 | 0.25 |
| Formaldehyde solution | 48.2 | 37.0 | 17.8 | 0.594 | 1.24 |
| Water (dilution) | 92.0 | | | | |
| Water (wash) | 57.0 | | | | |

Procedure

Concentrated filtrate and wash liquor (56.3 g, equivalent to 75% of the original quantity before removal of samples, containing moisture (9.6 g) and N-phosphonomethyliminodiacetic acid (5.8 g, 0.026 moles)) was charged with extra water (1.6 g, to make a total of 11.2 g, 0.622 moles) to the reaction flask described above, and phosphorous acid (39.7 g at 99%, 0.479 moles) was added. Sulphuric acid (25% replacement, i.e. 12.0 g at 98%, 0.5 moles) was added over 5 minutes, followed by iminodiacetic acid (66.5 g at 95.4%, 0.479 moles). The above procedure was then followed to yield 107.7 g of dry product at 95.4% strength equivalent to an isolated yield of 93.7%. The filtrate (153.4 g) and wash (72.8 g) contained 3.2% and 1.2% N-phosphonomethyliminodiacetic acid respectively; the total yield, minus the N-phosphonomethyliminodiacetic acid recycled with the filtrate, gave a stage conversion yield of 91.7%.

Cycles 3 to 11

The procedure as for Cycle 2 was repeated for Cycles 3 to 11, adjustments being made for the water content of the concentrated filtrates (equivalent to 75% recycle in each case) as follows:

| Cycle No. | Concentrated Filtrate + Wash Weight used g | Water content % | PIDA content % | Water Added g | Isolated Product Strength % | Isolated Product Yield % | Conversion Yield % |
|---|---|---|---|---|---|---|---|
| 3 | 53.0 | 12.3 | 8.5 | 4.7 | 96.6 | 99.4 | 95.8 |
| 4 | 49.8 | 12.9 | 3.5 | 4.8 | 96.6 | 91.7 | .3.7 |
| 5 | 53.0 | 11.1 | 4.9 | 5.4 | 99.8 | 91.7 | 95.8 |
| 6 | 58.9 | 12.3 | 6.1 | 4.0 | 93.8 | 83.3 | 87.5 |
| 7 | 63.6 | 8.8 | 8.4 | 5.6 | 90.6 | 87.5 | 86.3 |
| 8 | 62.4 | 8.7 | 5.2 | 5.8 | 96.4 | 90.2 | 91.9 |
| 9 | 64.5 | 9.4 | 5.9 | 5.1 | 96.1 | 89.6 | 89.6 |
| 10 | 66.9 | 8.6 | 5.9 | 5.4 | 94.2 | 87.5 | 87.5 |
| 11 | 66.6 | 7.2 | 4.9 | 6.4 | 90.4 | 87.5 | 87.5 |

EXAMPLE 7

Cycle 1

(Summary Table)

| MATERIAL | Actual Weight | Strength | 100% Weight | MOLES | MOLE RATIO |
|---|---|---|---|---|---|
| Iminodiacetic acid | 66.5 | 95.8 | 63.7 | 0.479 | 1 |
| Water | 11.2 | 100 | 11.2 | 0.622 | 1.3 |
| Phosphorous acid | 55.6 | 99.0 | 55.0 | 0.671 | 1.40 |
| Sulphuric acid | 49.8 | 98.0 | 48.8 | 0.498 | 1.04 |
| Formaldehyde solution | 48.2 | 37.0 | 17.8 | 0.594 | 1.24 |
| Water (dilution) | 92.0 | | | | |
| Water (wash) | 57.0 | | | | |

The procedure of Cycle 1 of Example 2 was followed using the above proportions.

The resultant slurry was filtered, washed with cold water (57.0 g) and the resulting product was dried at 60° C. in a vacuum oven overnight to give 104.0 g of N-phosphonomethyliminodiacetic acid at 99.0% strength, equivalent to an isolated yield of 94.7%. The filtrates (191.9 g) and the water wash (57.7 g) contained 2.0% and 1.24% N-phosphonomethyliminodiacetic acid respectively. This gave a total conversion yield of 99.0% N-phosphonomethyliminodiacetic acid.

The combined filtrates and wash liquors (243.0 g) were charged to a stirred 500 ml flask set up for vacuum distillation. The equipment wa evacuated to a pressure of 50 mm Hg and gradually warmed to distill off water until the flask temperature rose to 100° C. The residue (87.3 g) was cooled and analysed for N-phosphonomethyliminodiacetic acid (7.0%) and moisture content (16.8%).

Cycle 2 with 90% Acid Filtrates Recycle (Summary Table)

| MATERIAL | Actual Weight | Strength | 100% Weight | MOLES | MOLE RATIO |
|---|---|---|---|---|---|
| Concentrated filtrates | 80.7 | | | | |
| Iminodiacetic acid | 66.5 | 95.8 | 63.7 | 0.479 | 1 |
| Water: See text: To | 11.2 | 100 | 11.2 | 0.622 | 1.3 |
| Phosphorous acid | 39.7 | 99.0 | 39.3 | 0.479 | 1 |
| Sulphuric acid | 4.8 | 98.0 | 4.7 | 0.048 | 0.1 |
| Formaldehyde solution | 48.2 | 37.0 | 17.8 | 0.594 | 1.24 |
| Water (dilution) | 92.0 | | | | |
| Water (wash) | 57.0 | | | | |

Procedure

Concentrated filtrate and wash liquor (80.7 g, equivalent to 90% of the original quantity before removal of samples, containing moisture (13.6 g) and N-phosphonomethyliminodiacetic acid (5.65 g, 0.025 moles)) was charged to the reaction flask desccribed above, and phosphorous acid (39.7 g at 99%, 0.479 moles) was added. Sulphuric acid (10% replacement, i.e. 4.8 g at 98%, 0.048 moles) was added over 5 minutes, followed by iminodiacetic acid (66.5 g at 95.4%, 0.479 moles). The above procedure was then followed to yield 116.1 g of dry product at 92.8% strength equivalent to an isolated yield of 97.9%. The filtrate (142.6 g) and wash (66.0 g) contained 1.3% and 1.2% N-phosphonomethyliminodiacetic acid respectivvely; the total yield, minus the N-phosphonomethyliminodiacetic acid recycled with the filtrate, gave a stage conversion yield of 95.8%.

Cycles 3 to 6

The procedure as for Cycle 2 was repeated for Cycles 3 to 6, adjustments being made for the water content of the concentrated filtrates (equivalent to 90% recycle in each case) as follows:

| | Concentrated Filtrate + Wash | | | Water | Isolated Product | | Conversion |
|---|---|---|---|---|---|---|---|
| Cycle No. | Weight used g | Water content % | PIDA content % | Added g | Strength % | Yield % | Yield % |
| 3 | 72.8 | 16.8 | 4.3 | NIL | 93.2 | 93.7 | 93.7 |
| 4 | 71.9 | 16.2 | 3.0 | NIL | 95.0 | 95.8 | 95.8 |
| 5 | 68.4 | 13.0 | 2.9 | 2.3 | 90.1 | 89.6 | 89.6 |
| 6 | 68.4 | 12.0 | 2.7 | 3.0 | 93.5 | 87.5 | 89.6 |

We claim:

1. A process for the manufacture of N-phosphonomethyliminodiacetic acid which comprises:
   1) reacting iminodiacetic acid with phosphorous acid and a source of formaldehyde in aqueous solution in the presence of concentrated sulphuric acid;
   2) filtering and recovering the N-phosphonomethyliminodiacetic acid product precipitated in stage (1);
   3) recovering the filtrates from stage (2) and optionally removing a proportion of the water therefrom;
   4) transferring the filtrates from stage (3) to a further reaction stage in which further iminodiacetic acid is reacted with phosphorous acid and a source of formaldehyde in the presence of sulphuric acid; and thereafter
   5) repeating stages (1), (2), (3) and (4) in a plurality of re-cycles.

2. A process according to claim 1 wherein water is removed in stage (3).

3. A process according to claim 1 wherein there is used from 1 to 1.5 moles of phosphorous acid per mole of iminodiacetic acid.

4. A process according to claim 1 wherein there is used from 1 to 2 moles of formaldehyde per mole of iminodiacetic acid.

5. A process according to claim 1 wherein there is used from 0.5 to 2 moles of sulphuric acid per mole of iminodiacetic acid.

6. A process according to claim 1 wherein the reaction temperature of stage (1) is from 50° C. to 150° C.

* * * * *